United States Patent
De Villemeur et al.

(10) Patent No.: US 9,526,744 B2
(45) Date of Patent: Dec. 27, 2016

(54) METHOD FOR PRODUCING NO/$N_2$ GASEOUS MIXTURES INTENDED FOR THE MEDICAL FIELD

(71) Applicant: Air Liquide Santé (International), Paris (FR)

(72) Inventors: Pierre De Villemeur, Louveciennes (FR); Laurent Lecourt, Boulogne (FR)

(73) Assignee: L'Air Liquide, Société Anonyme our l'Etude et l'Exploitation des Procédés Georges Claude, Paris (FR)

( * ) Notice: Subject to any disclaimer, the term of this patent is extended or adjusted under 35 U.S.C. 154(b) by 83 days.

(21) Appl. No.: 14/302,282

(22) Filed: Jun. 11, 2014

(65) Prior Publication Data

US 2014/0370125 A1 Dec. 18, 2014

(30) Foreign Application Priority Data

Jun. 12, 2013 (FR) ...................................... 13 55404

(51) Int. Cl.
*A61K 33/00* (2006.01)
*C01B 21/24* (2006.01)
(Continued)

(52) U.S. Cl.
CPC ............. *A61K 33/00* (2013.01); *C01B 21/045* (2013.01); *C01B 21/0422* (2013.01);
(Continued)

(58) Field of Classification Search
CPC ................ C01B 21/04–21/0494; C01B 21/20; C01B 21/24; C01B 21/004; A61M 2202/0275; A61M 16/12; A61M 16/122; A61K 33/00
See application file for complete search history.

(56) References Cited

U.S. PATENT DOCUMENTS 4,713,224 A * 12/1987 Tamhankar ............ B01J 23/755
  423/219
4,717,406 A * 1/1988 Giacobbe ............... B01D 37/00
  62/46.1
(Continued)

FOREIGN PATENT DOCUMENTS

EP  0 240 270   10/1987
EP  2 533 125   12/2012

OTHER PUBLICATIONS

French Search Report for FR 1355404, Mar. 12, 2014.

*Primary Examiner* — Anthony J Zimmer
(74) *Attorney, Agent, or Firm* — Allen E. White

(57) ABSTRACT

The invention relates to a method for producing an NO/$N_2$ gaseous mixture, comprising the steps of effecting a purification of impure gaseous nitrogen containing impurities at least of the $O_2$ type by putting the impure nitrogen in contact with a catalyst and then with a molecular sieve; mixing the pure nitrogen obtained with nitric oxide (NO), and obtaining a mixture formed from NO and pure nitrogen containing an NO content of less than 20% by volume and a proportion of impurities of the $O_2$ type of less than 5 ppmv and of the $H_2O$ type of less than 40 ppmv. The NO/nitrogen mixture may undergo supplementary dilutions with pure nitrogen. Such NO/nitrogen mixtures can be used for treating, by inhalation, pulmonary vasoconstrictions in adults or children, in particular in new-born babies suffering from primitive pulmonary hypertension or in patients undergoing heart surgery.

11 Claims, 2 Drawing Sheets

(51) Int. Cl.
*C01B 21/04* (2006.01)
*A61M 16/12* (2006.01)
(52) U.S. Cl.
CPC .......... *C01B 21/0433* (2013.01); *C01B 21/24* (2013.01); *A61M 16/12* (2013.01); *A61M 2202/0266* (2013.01); *A61M 2202/0275* (2013.01); *A61M 2202/0283* (2013.01); *A61M 2207/00* (2013.01); *C01B 2210/001* (2013.01); *C01B 2210/0006* (2013.01); *C01B 2210/0045* (2013.01); *C01B 2210/0062* (2013.01)

(56) References Cited

U.S. PATENT DOCUMENTS

| | | |
|---|---|---|
| 4,869,883 A | 9/1989 | Thorogood et al. |
| 2012/0312417 A1 | 12/2012 | De Villemeur et al. |

\* cited by examiner

METHOD FOR PRODUCING NO/N$_2$ GASEOUS MIXTURES INTENDED FOR THE MEDICAL FIELD

CROSS REFERENCE TO RELATED APPLICATIONS

This application claims the benefit of priority under 35 U.S.C. §119(a) and (b) to French Application No. 1355404, filed Jun. 12, 2013, the entire contents of which are incorporated herein by reference.

BACKGROUND

The invention concerns a method for manufacturing an NO/N$_2$ gaseous mixture and subsequent packaging thereof in a receptacle, in particular in one or more gas bottles.

NO/N$_2$ gaseous mixtures are commonly used for treating pulmonary vasoconstrictions in adults, children and in particular new-born babies suffering from primitive pulmonary hypertension or in patients undergoing heart surgery.

These NO/N$_2$ mixtures are conventionally packaged in gas bottles made from steel and aluminium containing 100 to 1000 ppm by volume of NO and nitrogen (N$_2$) for the remainder. These bottles typically have a water-equivalent capacity of 2 to 50 liters.

The packaging, that is to say the bottling of these mixtures, is done in gas bottling centres. To do this, one or more mixtures of NO and nitrogen are produced until the required NO concentration in the nitrogen is obtained.

However, it may happen that the NO/nitrogen mixtures thus produced are not in accordance with the specifications of the medical field since they contain an excessively high quantity of impurities, in particular of the NO$_2$ type.

In other words, the reliability of the conventional methods for producing NO/N$_2$ mixtures is often haphazard.

However, the NO$_2$ impurities present in the final NO/nitrogen mixture produced pose a serious problem on a medical level since NO$_2$ is highly toxic when it is inhaled by a patient, even in very small doses, namely around a few ppm by volume.

The problem is consequently to propose an improved method for producing NO/N$_2$ gaseous mixtures ensuring good precision during the mixing of the gaseous compounds but also increased reliability and purity of the NO/N$_2$ gaseous mixture produced and then packaged, that is to say able to produce NO/nitrogen mixtures free or almost free from NO$_2$ impurities.

SUMMARY

The solution of the invention is then a method for producing an NO/N$_2$ gaseous mixture comprising the steps of:
a) carrying out a purification of impure gaseous nitrogen containing impurities at least of the O$_2$ type by:
  i) putting the impure nitrogen in contact with a catalyst in order to eliminate or convert at least some of the O$_2$-type impurities,
  ii) putting the nitrogen purified at substep i) in contact with a molecular sieve in order to eliminate at least some of the impurities of the H$_2$O type resulting from step i),
b) mixing the pure nitrogen resulting from step a) with nitric oxide (NO),
c) obtaining a mixture formed from NO and pure nitrogen containing an NO content of less than 20% by volume and a proportion of impurities of the O$_2$ type of less than 5 ppmv and of the H$_2$O type of less than 40 ppmv.

In the context of the present invention, the pressures given are absolute pressures and the proportions of gaseous compounds are given as % by volume (% v) or in ppm by volume, i.e. in ppmv.

According to the circumstances, the method of the invention may comprise one or more of the following technical features:
- at substep i), a nickel catalyst is used;
- in substep ii), a molecular sieve is used comprising a zeolite, an alumina or silica gel;
- it comprises a substep iii), in which a filter is used having a pore diameter of less than 100 μm, preferably less than or equal to 25 μm.
- substep iii) follows on from substep ii). It eliminates the solid particles, in particular issuing from and/or generated during substeps i) and/or ii), in particular particles of the dust type or residues resulting from an attrition of the molecular sieve;
- upstream of step a), the impure gaseous nitrogen is obtained by vaporisation of liquid nitrogen;
- at step c), a mixture formed from NO and pure nitrogen is obtained, containing a proportion of impurities of the O$_2$ type of less than 1 ppmv and/or of the H$_2$O type of less than 10 ppmv;
- step a) comprises a supplementary substep of passing the nitrogen purified at substep ii) through at least one filter in order to eliminate the solid particles, such as dust, etc.;
- the impure gaseous nitrogen contains less than 80 ppmv of O$_2$ impurities and/or less than 100 ppmv of H$_2$O impurities;
- the impure gaseous nitrogen contains less than 50 ppmv of O$_2$ impurities and/or less than 67 ppmv of H$_2$O impurities;
- the NO/N$_2$ mixture obtained at step c) contains an NO content of less than or equal to 10% by volume, preferably an NO content of less than or equal to 8% by volume, preferably again an NO content of less than or equal to 5% by volume, for example around 4% v;
- at step c), a mixture formed from NO and pure nitrogen is formed, containing an NO content of less than 5% by volume and a proportion of impurities of the O$_2$ type of less than 0.5 ppmv and/or of the H$_2$O type of less than 5 ppmv;
- at step c), a mixture formed from NO and pure nitrogen is formed, containing an NO content of less than 4% by volume and a proportion of impurities of the O$_2$ type of less than 0.1 ppmv and/or of the H$_2$O type of less than 3 ppmv;
- the NO/N$_2$ mixture obtained at step c) containing an NO content of less than or equal to 20% by volume undergoes an additional dilution with nitrogen so as to obtain a final NO/N$_2$ mixture containing an NO content of less than or equal to 5000 ppmv, preferably between 100 and 1000 ppmv;
- the final NO/N$_2$ mixture containing an NO content of less than or equal to 5000 ppmv, preferably between 100 and 1000 ppmv, is packaged in one or more gas storage containers, in particular gas cylinders, especially gas cylinders having a water-equivalent capacity of 2 to 50 liters;
- at step c), the gaseous mixture formed from NO and N$_2$ contains an NO content of less than or equal to 8% by volume;

at step c), the gaseous mixture formed from NO and $N_2$ contains an NO content of less than or equal to 5% by volume;

at step c), the gaseous mixture formed from NO and $N_2$ contains an NO content of around 4% by volume;

the final gaseous mixture formed from NO and $NO_2$ contains for example, after dilution with pure nitrogen, 450 ppmv of NO (+/−5%), less than 3 ppmv of $NO_2$, and nitrogen for the remainder, and optionally less than 50 ppmv of $N_2O$, and/or less than 450 ppmv of $CO_2$.

BRIEF DESCRIPTION OF THE DRAWINGS

The invention will now be understood better by means of the description given below with reference to the accompanying figures, among which.

DESCRIPTION OF PREFERRED EMBODIMENTS

Figure 1:
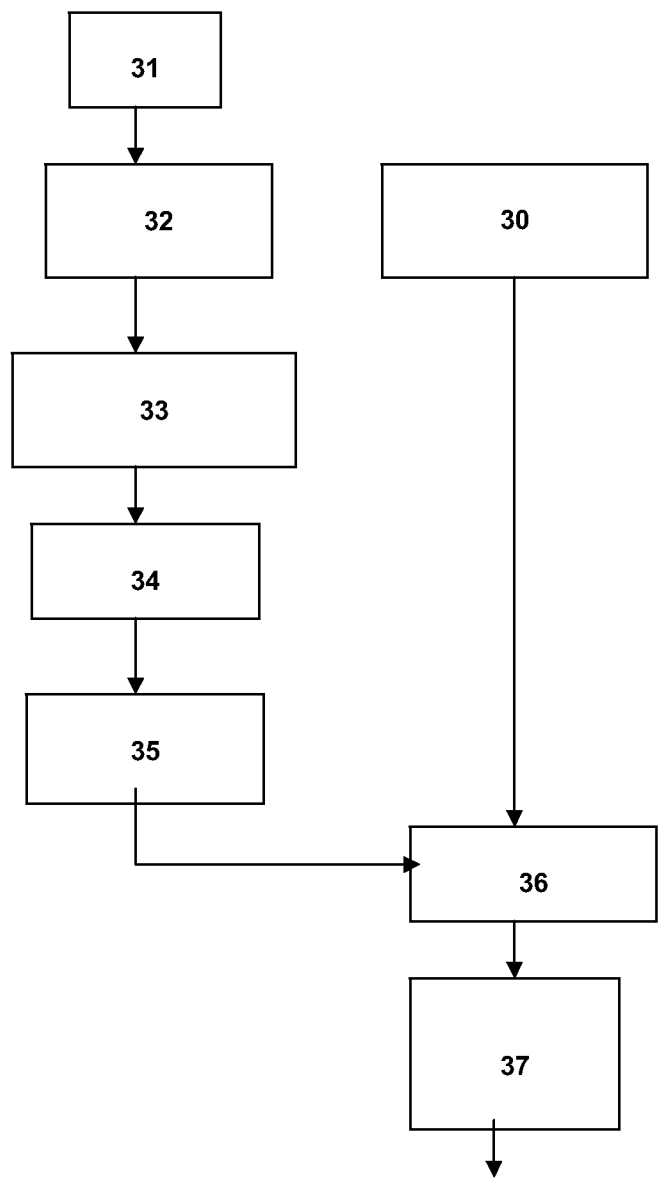
FIG. 1 shows schematically an embodiment of the method according to the present invention.

FIG. 1 shows schematically an embodiment of the production method according to the present invention, which produces $NO/N_2$ gaseous mixtures free or almost free from $NO_2$ impurities, for example $NO/N_2$ gaseous mixtures containing approximately 4% NO and nitrogen for the remainder.

According to this method, the following successive steps are performed:

impure nitrogen is supplied (at 31) having the following composition: $O_2 \leq 50$ ppmv, $CO \leq 5$ ppmv, $CO_2 \leq 300$ ppmv, $H_2O \leq 67$ ppmv and $N_2$ for the remainder (approx. 99.5% v)

purification of the impure gaseous nitrogen containing said above impurities is carried out by:

i) putting (at 32) the impure nitrogen in contact with a nickel catalyst for example in order to eliminate or convert at least some of the impurities of the $O_2$ type, in particular to convert them into water vapour or $H_2O$, ii) putting the nitrogen purified at substep i) in contact (at 33) with a molecular sieve, such as a 10 A° zeolite, in order to eliminate at least some of the $H_2O$-type impurities, either initially present in the nitrogen supplied at 31, or resulting from the conversion of the $O_2$ impurities of step i) (at 32), iii) the nitrogen issuing from step ii) is filtered (at 34) in order to eliminate therefrom any solid particles, such as dust resulting from wear by friction or attrition of the molecular sieve particles during step ii), the purified nitrogen with its gaseous impurities of the $O_2$ and $H_2O$ type removed is recovered (at 35), in particular nitrogen containing at a maximum 200 ppbv of $O_2$ impurities, preferably less than 100 ppbv of $O_2$, and at a maximum 1 ppmv of $H_2O$ impurities. The analysis of these impurities is carried out continuously, nitric oxide or pure NO (at 30) issuing from a source of NO, such as a storage tank (not shown), is supplied, the purified nitrogen issuing from step a) is mixed (at 36) with the pure NO, for example in a gas mixture, a mixture formed from NO and pure nitrogen is obtained, containing an NO content of 20% v, typically around 4% v, and a proportion of the $O_2$ type of less than approximately 1 ppmv and of the $H_2O$ type of less than approximately 10 ppmv.

Next, the NO and pure nitrogen mixture containing an NO content of less than or equal to 20% by volume, typically around 3% to 10% by volume, preferentially around 4% by volume, may undergo one or more supplementary dilutions in order to reduce the NO content in the final mixture, for example in order to produce an $NO/N_2$ mixture devoid of gaseous impurities of the $O_2$, $H_2O$ and $NO_2$ type, and containing a proportion of NO of between 100 and 5000 ppmv, typically less than 1000 ppmv, which can be packaged in gas bottles thereafter, as explained below.

Figure 2:
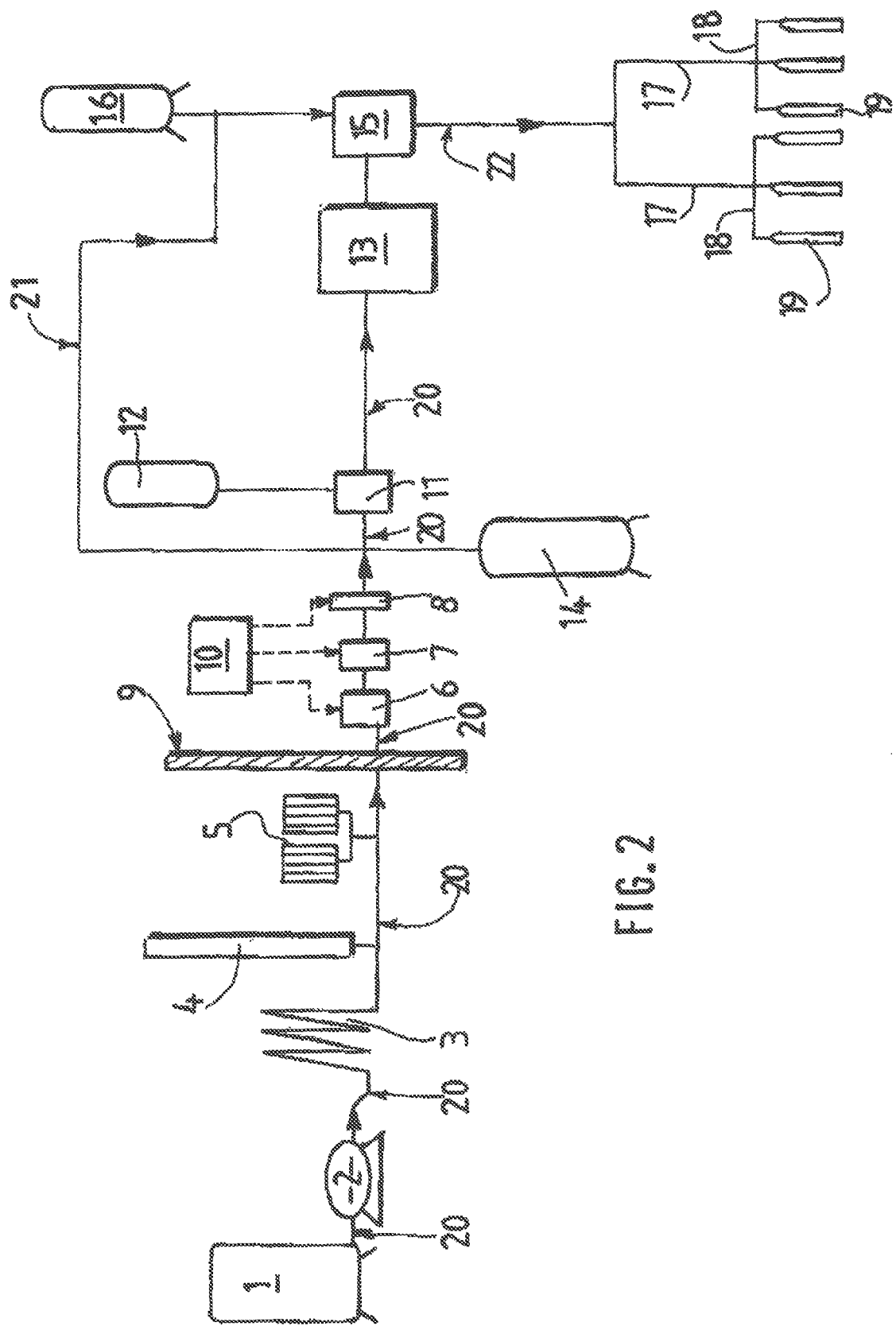
FIG. 2 shows the diagram of an installation for implementing the method of the invention.

The method according to the invention illustrated in FIG. 1 can be implemented by means of an installation as shown schematically in FIG. 2.

Impure nitrogen containing at least residual impurities of the $O_2$ type is stored in a tank 1 in liquid form and then drawn off in liquid form by a cryogenic pump 2, which compresses it to a pressure of around 100 to 300 bar, before sending it to an atmospheric heater 3, where it is vaporised so as to obtain impure gaseous nitrogen.

As can be seen, it comprises a main pipe or line 20 conveying the impure nitrogen from the tank 1 as far as a tank 13 containing the $NO/N_2$ mixture to be produced.

It should be noted that the line 20 can also be fluidically connected to a buffer tank 4 for storing part of the impure gaseous nitrogen issuing from the heater 3, as well as backup frames 5 each comprising several bottles of impure nitrogen serving as a backup $N_2$ source taking over to supply impure nitrogen in the event of malfunctioning of the upstream part of the installation, in particular the pump 2 or heater 3.

The above elements of the installation are preferentially situated outside a building 9.

In fact, the impure gaseous nitrogen issuing from the atmospheric heater 3, the buffer tank 4 or the backup frames 5 is then conveyed by the line 20 to a purification system 6, 7, 8 eliminating, according to the invention, the $O_2$ and $H_2O$ impurities that form residual impurities in the gaseous impure nitrogen.

These $O_2$ and $H_2O$ impurities must absolutely be eliminated since it is they that are responsible for the formation of toxic $NO_2$ in the final $NO/N_2$ mixture stored in the tank 13. This is because, after mixing of the nitrogen with the NO (at 11), the $O_2$ and $H_2O$ impurities will react with the NO in order to oxidise it and thus form the toxic species of the $NO_2$ type.

Therefore, by acting upstream of the installation, that is to say before the mixing of the NO with the nitrogen that takes place in the mixer 11, it is possible to prevent this phenomenon and obtain final $NO/N_2$ mixtures free from $O_2$ and $H_2O$ impurities, and thus therefore also free from toxic species of the $NO_2$.

More precisely, the purification system 6, 7, 8 comprises, according to the invention, at least one catalytic chamber 6 and at least one adsorber 7, and preferably at least one filtration compartment 8, arranged in series, as illustrated in FIG. 2.

A control device 10, such as a control cubicle with programmable automatic controller or the like, controls the purification system 6, 7, 8 by acting in particular on valves (not shown) that control the gas inlets and outlets to and from the catalytic chamber 6, the adsorber 7 and the filtration compartment 8. This type of control device 10 is conventional and will not be detailed below.

According to a preferred embodiment, the purification system 6, 7, 8 comprises:

a catalytic chamber 6 containing a catalyst, preferably a nickel catalyst, for converting the $O_2$ species present in the impure nitrogen issuing from the heater 3, the buffer tank 4 or the backup frames 5, into $H_2O$ species;

one (or more) adsorber 7 containing at least one molecular sieve, for example of the zeolite, silica gel, alumina or similar type, or mixtures thereof. This molecular sieve eliminates the $H_2O$ species either present from the start in the impure nitrogen issuing from the tank 1, or produced during the conversion of the $O_2$ impurities in the catalytic chamber 6;

a filtration compartment 8 comprising at least one filter with a pore diameter preferentially less than 100 μm, typically around 25 μm, stopping in particular the solid residues liable to be released in the adsorber 7 because of the attrition of the molecular sieve particles under the effect of variations in pressure and gas flows treated.

The adsorber or adsorbers 7 can function in PSA (pressure swing adsorption) mode, in VSA (vacuum swing adsorption) mode or in TSA (temperature swing adsorption) mode for example, and therefore with conventional phases of regenerating by pressure, vacuum or temperature variation. This type of adsorption method is known to persons skilled in the art and does not need to be detailed in the context of the present invention.

Likewise, the catalytic chamber 6 can be periodically generated by a hot gas for example. There also, this type of catalysis and regeneration method is known to persons skilled in the art and does not need to be detailed in the context of the present invention.

It should be noted moreover that other catalysts can also be suitable, for example platinum or palladium catalyst. Likewise, the molecular sieve may be of the non-zeolitic type, for example activated alumina or silica gel. A person skilled in the art is capable, via routine tests, to select the catalyst or catalysts and the adsorbents that are most suitable, as well as one or more suitable filters.

Once its impurities have been removed, the purified nitrogen can be stored in a storage tank 14 or be conveyed directly by the line 20 to a mixing device or mixer 11, which is also supplied by a source of pure NO 12, so as to effect therein the mixing of NO and purifying nitrogen in the required proportions, for example an $NO/N_2$ mixture containing approximately 4% NO.

This mixture of NO and purified nitrogen can then be stored in a second storage tank 13 before being sent, via a line supplying the manifolds 22 and secondary gas lines 17 branching from the line supplying the manifolds 22, to packaging manifolds 18, where it can be put in gas bottles 19.

However, before packaging the $NO/N_2$ mixture in gas bottles 19, it may be useful or even necessary to adjust the NO content, in particular to reduce it to a required final use content, for example a final content of NO of between 100 and 5000 ppmv, typically less than 1000 ppmv.

To do this, provision can be made for effecting an additional dilution of the $NO/N_2$ mixture in a second mixing device 15 with pure nitrogen, so as to reduce the NO content in the $NO/N_2$ mixture and thus to obtain a final $NO/N_2$ mixture containing between 200 and 5000 ppmv of NO, the remainder being nitrogen, typically between 200 and 1000 ppmv.

The second mixing device 15 is arranged downstream of the first mixer 11 and of the storage tank 13. It is moreover supplied with pure nitrogen that is used to dilute the $NO/N_2$ mixture and issues from a storage tank 16 that can be supplied with purified nitrogen conveyed by a bypass line 21 connected to the main line 20, downstream of the purification system 6, 7, 8, as illustrated in FIG. 2.

The gas bottles 19 are of the type with a steel, aluminium or aluminium alloy body, and have a capacity (water equivalent) of between 2 and 50 liters approximately. The gaseous mixture is stored therein at a pressure ranging up to 300 bar.

It should be noted that flow meters (not shown) may be provided to measure the quantity of $N_2$ and NO flowing in the gas supply lines, in particular the main line 20, the bypass line 21 or the line supplying the manifolds 22, and to transmit the measured information to the control device 10 or to any other device controlling the installation, such as computer or the like.

EXAMPLE

An installation similar to the one in FIG. 2 was used to implement the method of FIG. 1 so as to test the efficacy of the solution proposed by the present invention in the production of an $NO/N_2$, gaseous mixture containing approximately 4% NO and devoid of toxic impurities of the $NO_2$ type.

The conditions of the method are given in Table 1 below.

TABLE 1

| | |
|---|---|
| Initial $O_2$ content in the impure nitrogen | ≤50 ppmv |
| Initial $H_2O$ content in the impure nitrogen | ≤67 ppmv |
| Ni-1404 T 3/16" catalyst | nickel (68%) |
| Molecular sieve (adsorbent) | 10 A° zeolite |
| Type of filter (pore diameter) | 25 μm |
| $O_2$ content in the purified nitrogen | <0.1 ppmv approx. |
| $H_2O$ content in the purified nitrogen | <3 ppmv approx. |
| $NO/N_2$ mixture obtained | NO: 3.8 to 4.2% vol. |
| | $NO_2$: approx. 0 ppmv |
| | Nitrogen: remainder |
| Final $NO/N_2$ mixture after additional dilution with pure nitrogen (several different mixtures were produced) | NO: 200 to 1000 ppmv |
| | $NO_2$: approx. 0 ppmv |
| | Nitrogen: remainder |

Table 2 below gives the characteristics of the catalyst used to stop the $O_2$-type impurities and to convert them into $H_2O$ in particular.

TABLE 2

| | |
|---|---|
| Name of catalyst | Ni-1404 T 3/16" |
| Manufacturer | Engelhard |
| Catalyst metal | Nickel |
| Nickel content | 68% by weight |
| Surface area | 130 m$^2$/g |
| Total pore volume | 0.38 cc/g |
| Side crush strength | 7.5 kg |
| Reduced value ratio | 0.55 |
| Type of catalyst | hydrogenation |
| Form of catalyst | particles |

Table 3 below gives the characteristics of the molecular sieve used to stop the impurities of the $H_2O$ type (water vapour).

TABLE 3

| | |
|---|---|
| Molecular sieve | zeolite |
| Manufacturer | Grace |
| Type | 544 |
| Pore size | 10 A° |
| Granulometry | 1.6-2.5 mm |
| Apparent density | 670 g/l |
| Water adsorption capacity | 22% by weight |
| Form of the adsorbent | particles |

The filter used to stop the solid particles, for example the dust resulting from the attrition of the molecular sieve, has a mean pore diameter of around 25 μm.

In the light of the results given in Table 1, it is found that the method of the invention is effective since it makes it possible to eliminate the major part of the $O_2$ and $H_2O$ impurities liable to be present in the impure nitrogen and thus to obtain an $NO/N_2$ mixture containing a final proportion of $H_2O$ less than approximately 3 ppmv and a final proportion of $O_2$ less than approximately 0.1 ppmv, leading to an almost zero formation of toxic $NO_2$ in the final mixture.

The $NO/N_2$ gaseous mixtures thus produced can be used to treat, by inhalation, pulmonary vasoconstrictions in adults and children, in particular in new-born babies suffering from primitive pulmonary hypertension or in patients undergoing heart surgery.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

The invention claimed is:

1. A method for producing an $NO/N_2$ gaseous mixture, comprising the steps of:
   a) carrying out a purification of impure gaseous nitrogen containing $O_2$ impurities by:
      i) putting the impure nitrogen in contact with a nickel catalyst in order to convert at least some of the $O_2$ impurities to $H_2O$,
      ii) putting the nitrogen purified at substep i) in contact with a molecular sieve in order to eliminate at least some of the $H_2O$ resulting from step i),
   b) mixing the pure nitrogen resulting from step a) with nitric oxide (NO),
   c) obtaining a mixture formed from NO and pure nitrogen containing an NO content of less than 20% by volume and $O_2$ at less than 5 ppmv and $H_2O$ at less than 40 ppmv.

2. The method according to claim 1, wherein at step a), substep ii), the molecular sieve contains a zeolite, an alumina or a silica gel.

3. The method according to claim 1, wherein step a) further comprises a substep iii) in which the nitrogen gas of step ii) is filtered thru a filter having a pore diameter of less than 100 μm.

4. The method according to claim 1, wherein upstream of step a), the impure gaseous nitrogen is obtained by vaporisation of liquid nitrogen.

5. The method according to claim 1, wherein the $O_2$ is less than 1 ppmv and/or the $H_2O$ is less than 10 ppmv in the mixture of step c).

6. The method according to claim 1, wherein the impure gaseous nitrogen contains less than 80 ppmv of $O_2$ and less than 100 ppmv of $H_2O$.

7. The method according to claim 1, wherein the $NO/N_2$ mixture obtained at step c) contains an NO content of less than or equal to 10% by volume.

8. The method according to claim 1, wherein at step c), a mixture formed from NO and pure nitrogen is obtained, containing a) an NO content of less than 5% by volume and b) $O_2$ less than 0.5 ppmv and/or $H_2O$ less than 5 ppmv.

9. The method according to claim 1, wherein at step c), a mixture formed from NO and pure nitrogen is obtained, containing a) an NO content of less than 4% by volume and b) $O_2$ less than 0.1 ppmv and/or $H_2O$ less than 3 ppmv.

10. The method according to claim 1, further comprising step d) a supplementary dilution with nitrogen so as to obtain a final $NO/N_2$ mixture containing an NO content of less than or equal to 5000 ppmv.

11. The method according to claim 1, wherein the final $NO/N_2$ mixture contains an NO content of less than or equal to 5000 ppmv, further comprising a step of packaging the final $NO/N_2$ mixture in one or more gas storage containers.

* * * * *